United States Patent [19]

Igarashi et al.

[11] Patent Number: 4,931,216
[45] Date of Patent: Jun. 5, 1990

[54] DETERGENT COMPOSITION COMPRISING AN ANIONIC OR AMPHOTERIC SURFACE ACTIVE AGENT AND A BRANCHED QUATERNARY AMMONIUM SALT

[75] Inventors: Sahoko Igarashi, Tokyo; Hidekazu Ogino, Koutoubashi; Hajime Hirota, Tokyo, all of Japan

[73] Assignee: Kao Corporation, Tokyo, Japan

[21] Appl. No.: 263,351

[22] Filed: Oct. 27, 1988

[30] Foreign Application Priority Data

Oct. 29, 1987 [JP] Japan .................. 62-274054
Jan. 20, 1988 [JP] Japan .................. 63-10291

[51] Int. Cl.$^5$ .................. C11D 1/65; C11D 3/37
[52] U.S. Cl. .................. 252/547; 252/8.75; 252/8.8; 252/542; 252/546; 252/74.23; 252/DIG. 2; 252/DIG. 14; 252/DIG. 13; 424/70
[58] Field of Search ....... 252/546, 547, 551, DIG. 13, 252/DIG. 14, DIG. 2

[56] References Cited

U.S. PATENT DOCUMENTS

| | | | |
|---|---|---|---|
| 3,990,991 | 11/1976 | Gerstein | 252/542 |
| 4,080,310 | 3/1978 | Ng et al. | 252/544 |
| 4,132,678 | 1/1979 | Iijima et al. | 252/545 |
| 4,214,998 | 7/1980 | Joy | 252/8.8 |
| 4,220,548 | 9/1980 | Hashimoto | 252/106 |
| 4,450,174 | 5/1984 | Green | 424/329 |
| 4,534,877 | 8/1985 | Russell | 252/106 |
| 4,578,216 | 3/1986 | Fujii et al. | 252/542 |
| 4,704,272 | 11/1987 | Oh et al. | 424/70 |

FOREIGN PATENT DOCUMENTS

2341592 2/1975 Fed. Rep. of Germany .

Primary Examiner—Prince E. Willis
Attorney, Agent, or Firm—Oblon, Spivak, McClelland, Maier & Neustadt

[57] ABSTRACT

A detergent composition is disclosed, which comprises (A) 0.1 to 40% by weight of at least one kind of anionic or amphoteric surface active agents and (B) 0.05 to 4% by weight of at least one kind of quaternary ammonium salts represented by the following formula (I) or (II):

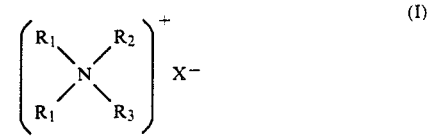

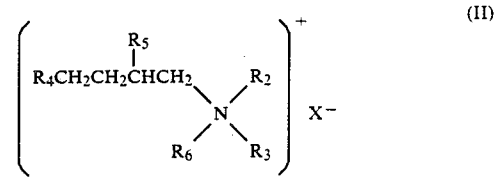

wherein $R_1$ represents a mixture of (a) a branched alkyl group represented by

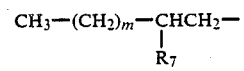

and (b) a linear alkyl group represented by $CH_3-(CH_2)_n-$ wherein $R_7$ represents a methyl or ethyl group, m is an integer to make the carbon atom content of the branched alkyl group to 8 to 16, and n is an integer of 7 to 15), with a ratio (a)/(a)+(b) being 0.1 to 1, $R_2$ and $R_3$ independently represent a benzyl group, an alkyl group having 1 to 3 carbon atoms, or a hydroxyalkyl group having 1 to 3 carbon atoms, $R_4$ and $R_5$ independently represent an alkyl group having 2 to 12 carbon atoms, $R_6$ represents a group

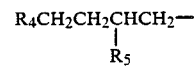

or an alkyl group having 1 to 3 carbon atoms, and $X^-$ represents a halogen ion or an organic anion. The detergent composition provides a shampoo with superb hair conditioning effects; softness and smoothness after washing, less sticky feeling, easy passage of comb through the hair, less hard or rough feeling as well as easy hair-set performance after drying. The detergent composition also provides a liquid detergent suitable for washing cloths made of wool or made of fine denier fibers.

3 Claims, No Drawings

DETERGENT COMPOSITION COMPRISING AN ANIONIC OR AMPHOTERIC SURFACE ACTIVE AGENT AND A BRANCHED QUATERNARY AMMONIUM SALT

BACKGROUND OF THE INVENTION

1. Field of the Invention:

This invention relates to a detergent composition, and, more particularly, to a detergent composition comprising an anionic or amphoteric surface active agent and a branched quaternary ammonium salt. The detergent composition is suitable for use as a shampoo, which provides superb hair conditioning effects, including softness and smoothness after washing, easy hair-set after drying, less sticky feeling, easiness of comb or finger passage through the hair. The detergent composition also provides a liquid detergent for washing cloths, which ensures softness of the cloths, especially those made of keratin fibers such as wool or the like, or made of fine denier fibers, after washing.

2. Description of the Background:

Many types of detergent compositions are commercially sold in recent years, which contain a cationic polymer such as a cationic cellulose, or a cationic surface active agent, in order to provide the washed hair with excellent conditioning effects or for the purpose of giving cloths an excellent soft feeling after washing. Most of these detergents can provide good softness to the hair or cloths after washing.

These conventional detergents, however, have drawbacks of poor detergent capability and insufficient softness of the hair or the cloths after drying because of cationic polymers or cationic surface active agents used in the detergents. More specifically, detergents for cloths into which a cationic surface active agent is formulated exhibit rather poor dirt-elimination capability due to an adverse effect of the cationic surfactant. Even though such a cationic surface active agent is employed in an amount small enough not to impair the detergent capability of the composition, softness of the finished cloths is still to be improved. Shampoos containing a cationic surface active agent tend to impart a sticky feel when the hair is dried after washing and to adversely affect a smooth passage of comb through the hair. In addition, a complex of a surface active agent and a cationic polymer solidifies in the course of hair drying and causes hair-fly or hardens the hair, thus providing insufficient conditioning effects. The use of increased amount of cationic polymer to eliminate these drawbacks brings about more stickiness and damages a smoothness or softness of the finished hair.

Because of this, there has been a strong desire for the development of a detergent which can provide an excellent conditioning effect to the hair or the cloths after washing and drying, specifically, providing softness, smoothness, and fine delicate feeling to the finished hair or the cloths.

The present inventors have undertaken extensive studies for the resolution of the above drawbacks in the conventional detergents, and found that a detergent composition to which a branched quaternary ammonium salt is formulated, in addition to an anionic or amphoteric surface active agent, gives a delicate softness to cloths after washing and provides soft, smooth feeling to the hair, eliminating the drawbacks of conventional shampoo compositions to which a cationic polymer is formulated, e.g. imparting stickiness in the course of drying or producing hardened hair after drying.

SUMMARY OF THE INVENTION

Accordingly, an object of this invention is to provide a detergent composition comprising:

(A) 0.1 to 40% by weight of at least one kind of anionic or amphoteric surface active agents and (B) 0.05 to 4% by weight of at least one kind of quaternary ammonium salts represented by the following formula (I) or (II):

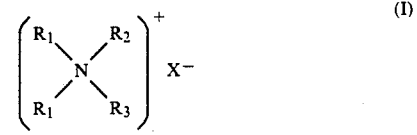

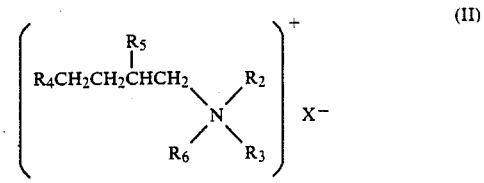

wherein $R_1$ represents a mixture of (a) a branched alkyl group represented by

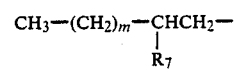

and (b) a linear alkyl group represented by $CH_3-(CH_2)_n-$ (wherein $R_7$ represents a methyl or ethyl group, m is an integer to make the carbon atom content of the branched alkyl group to 8 to 16, and n is an integer of 7 to 15), with a ratio (a)/(a)+(b) being 0.1 to 1, $R_2$ and $R_3$ independently represent a benzyl group, an alkyl group having 1 to 3 carbon atoms, or a hydroxyalkyl group having 1 to 3 carbon atoms, $R_4$ and $R_5$ independently represent an alkyl group having 2 to 12 carbon atoms, $R_6$ represents a group

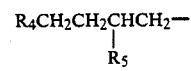

or an alkyl group having 1 to 3 carbon atoms, and $X^-$ represents a halogen ion or an organic anion.

Another object of this invention is to provide a detergent composition comprising, in addition to the above (A) and (B) components, (C) 0.05 to 2% by weight of at least one cationic polymer selected from the group consisting of cationized cellulose derivatives, cationic starch, copolymers of a diallyl quaternary ammonium salt and an acrylamide, quaternarized polyvinylpyrrolidone derivatives, and polyglycol-polyamine condensates.

It is more specific object of the present invention to provide a detergent composition, wherein 0.1 to 25% by weight, based on the detergent composition, of said (A) component is one or more amidoamine-type amphoteric surface active agents represented by the following formula (III) or (IV):

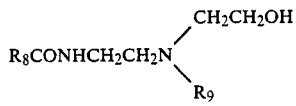

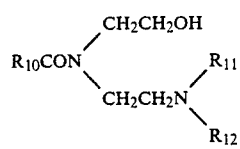

wherein $R_8$ and $R_{10}$ each independently represent a saturated or unsaturated hydrocarbon group having 7 to 19 carbon atoms, $R_9$ and $R_{11}$ each independently represent a group —$CH_2COOM$ or —$CH_2CH_2COOM$ (wherein M stands for a hydrogen atom, an alkali metal, or an alkanol amine), $R_{12}$ represents a hydrogen atom, a group —$CH_2COOM$, or a group —$CH_2CH_2COOM$ (wherein M has the same meaning as defined above).

Other objects, features and advantages of the invention will hereinafter become more readily apparent from the following description.

DETAILED DESCRIPTION OF THE INVENTION AND PREFERRED EMBODIMENTS

Following anionic and amphoteric surface active agents can be used as the (A) component surfactant:

Anionic surface active agent (1) Linear or branched alkyl benzene sulfonates having an alkyl group of an average carbon atom content of 10 to 16.

(2) Alkyl- or alkenylether sulfates having a linear or branched, alkyl or alkenyl group of an average carbon atom content of 10 to 20 and having, in a molecule, 0.5 to 8 mols of ethylene oxide adduct, propylene oxide adduct, butylene oxide adduct, ethylene oxide-propylene oxide adduct with a ratio of ethylene oxide/propylene oxide being 0.1/9.9 to 9.9/0.1, or ethylene oxide-butylene oxide adduct with a ratio of ethylene oxide/butylene oxide being 0.1/9.9 to 9.9/0.1.

(3) Alkyl- or alkenylether sulfates having an alkyl or alkenyl group of an average carbon atom content of 10 to 20.

(4) Olefin sulfonates having an average carbon atom content of 10 to 20 in a molecule.

(5) Alkane sulfonates having an average carbon atom content of 10 to 20 in a molecule.

(6) Saturated or unsaturated fatty acids having an average carbon atom content of 10 to 24.

(7) Alkyl- or alkenylether carboxylates having an alkyl or alkenyl group of an average carbon atom content of 10 to 20 and having, in a molecule, 0.5 to 8 mols ethylene oxide adduct, propylene oxide adduct, butylene oxide adduct, ethylene oxide-propylene oxide adduct with a ratio of ethylene oxide/propylene oxide being 0.1/9.9 to 9.9/0.1, or ethylene oxide-butylene oxide adduct with a ratio of ethylene oxide/butylene oxide being 0.1/9.9 to 9.9/0.1.

(8) α-fatty acid sulfonates or their esters having an alkyl or alkenyl group of an average carbon atom content of 10 to 20.

(9) N-acylamino acid-type surface active agents having an acyl group of an 8 to 24 carbon atom content and a free carboxylic acid radical.

(10) Mono- or diesters of phosphoric acid-type surface active agents having an alkyl or alkenyl group of an 8 to 24 carbon atom content.

Amphoteric surface active agent

(11) Imidazoline-type amphoteric surface active agents of α-position addition-type, secondary amido-type, or tertiary amido-type, having an alkyl, alkenyl, or acyl group of an 8 to 24 carbon atom content.

(12) Carbo-betaine-type, amido-betaine-type, sulfo-betaine-type, hydroxy-sulfo-betaine-type, or amidosulfo-betaine-type amphoteric surface active agents having an alkyl, alkenyl, or acyl group of an 8 to 24 carbon atom content.

Given as counter-ions for the anionic residual group of these surface active agents are alkali metal ions such as sodium or potassium ion, alkali earth metal ions such as calcium or magnesium ions, ammonium ion, alkanol amine ions having 1 to 3 alkanol groups with a 2 or 3 carbon atom content such as monoethanolamine, diethanolamine, triethanolamine, tri-i-propanolamine, and the like.

When these types of salts are used, the surface active agent tends to contain inorganic salts as contaminants. It is desirable that such inorganic salts be removed from the surface active agent so that the content of the inorganic salt contaminants in the final detergent product be less than 1% by weight.

Counter ions for cationic groups may be halogen ions such as chlorine, bromine, or iodine, methosulfate ion, succharinate ion, or the like.

Among these surface active agents preferable ones for use as a major detergent component are (2) alkylether sulfates, (3) alkyl sulfates, (4) olefin sulfonates, (6) saturated or unsaturated fatty acid salt-type anionic surface active agents, and (11) secondary or tertiary amido-type or imidazoline-type amphoteric surface active agents. Given as specific examples of suitable anionic surface active agents are sodium polyoxyethylenelaurylether sulfate (ethylene oxide addition: 2–3 mols in average) triethanolamine lauryl sulfate, sodium α-olefin sulfonate (average carbon atom content: 12–14), sodium salt of tallow/coconut (80/20) oil fatty acids, and the like.

Amido-amine type compounds represented by the following formula (III) or (IV) are given as examples of suitable amphoteric surface active agents.

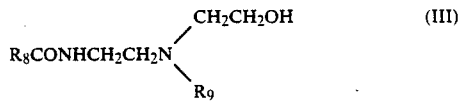

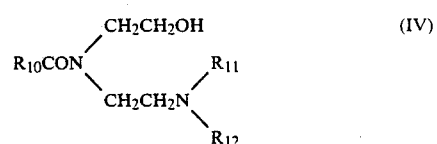

wherein $R_8$ and $R_{10}$ each independently represent a saturated or unsaturated hydrocarbon group having 7 to 19 carbon atoms, $R_9$ and $R_{11}$ each independently represent a group —$CH_2COOM$ or —$CH_2CH_2COOM$ (wherein M stands for a hydrogen atom, an alkali metal, or an alkanol amine), $R_{12}$ represents a hydrogen atom, a group —$CH_2COOM$, or a group —$CH_2CH_2COOM$ (wherein M has the same meaning as defined above).

Specific examples of suitable amido-amine type surface active agents represented by the formula (III) include N-lauroyl-N'-carboxymethyl-N'-(2-hydroxyethyl)ethylenediamine, N-lauroyl-N'-carboxyethyl-N'-(2-hydroxyethyl)ethylenediamine, N-myristoyl-N'-carboxymethyl-N'-(2-hydroxyethyl)ethylenediamine, N-myristoyl-N'-carboxymethyl-N'-(2-hydroxyethyl)ethylenediamine, N-palmitoyl-N'-carboxymethyl-N'-(2-hydroxyethyl)ethylenediamine, N-palmitoyl-N'-carboxyethyl-N'-(2-hydroxyethyl)ethylenediamine, and the like as well as their salts. Given as specific examples of suitable amido-amine type surface active agents represented by the formula (IV) are N-lauroyl-N-(2-hydroxyethyl)-N'-carboxymethylethylenediamine, N-lauroyl-N-(2-hydroxyethyl)-N',N'-bis(carboxymethyl)ethylenediamine, N-lauroyl-N-(2-hydroxyethyl)-N',N'-bis(carboxyethyl)ethylenediamine, N-myristoyl-N-(2-hydroxyethyl)-N'-carboxymethylethylenediamine, N-myristoyl-N-(2-hydroxyethyl)-N',N'-bis(carboxymethyl)ethylenediamine, N-myristoyl-N-(2-hydroxyethyl)-N',N'-bis(carboxyethyl)ethylenediamine, N-palmitoyl-N-(2-hydroxyethyl)-N'-carboxymethylethylenediamine, N-palmitoyl-N-(2-hydroxyethyl)-N',N'-bis(carboxymethyl)ethylenediamine, N-palmitoyl-N-(2-hydroxyethyl)-N',N'-bis(carboxyethyl)ethylenediamine, and the like as well as their salts.

Surface active agents may be used either individually or in combination with one or more other surface active agents.

Among the (B) components, branched quaternary ammonium salts represented by the general formula (I) are produced, for example, from oxo alcohols having an 8 to 16 carbon atom content. Specific examples are dialkyldimethylammonium salt, dialkylmethylhydroxyethylammonium salt, or dialkylmethylbenzylammonium salt, all having an alkyl group derived from an oxo alcohol. Counter ions for these ammonium salts may be a halogen ion such as chlorine ion, bromine ion, or iodine ion, or an organic anion such as methosulfate, ethosulfate, methophosphate, ethophosphate, or the like.

The alkyl group, $R_1$ in formula (I), is a group comprised of (a) a group represented by

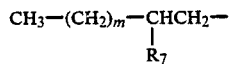

(wherein $R_7$ represents a methyl or ethyl group) and (b) a group represented by $CH_3-(CH_2)_n-$, both having an 8 to 18 carbon atom content. "Branched ratio" for $R_1$, (a)/(a)+(b), is usually in the range of 0.1 to 1, and particularly preferably in the range of 0.1 to 0.5. Although the total carbon number of the alkyl group $R_1$ may be 8 to 16, preferable groups ar those having a certain distribution of the carbon atom content.

$C_8$-$C_{11}$: less than 5%
$C_{12}$: 10-35%
$C_{13}$: 15-40%
$C_{14}$: 20-45%
$C_{15}$: 5-30%
$C_{16}$: less than 5%

Specific examples of particularly preferable branched quaternary ammonium salts represented by formula (I) are dialkyldimethylammonium chloride in which the alkyl group $R_1$ has 8 to 16 carbon atoms and a branched ratio is 0.1 to 0.5.

A branched quaternary ammonium salt represented by formula (II), which is the (B) component of the present invention, can be synthesized, for example, using as a raw material a Guerbet alcohol

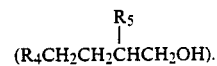

Given as preferable examples of this branched quaternary ammonium salt are monoalkyl-type quaternary salts such as alkyltrimethylammonium salt, alkyldimethylhydroxyethylammonium salt, and alkyldimethylbenzylammonium salt; dialkyldimethylammonium salt, dialkylmethylhydroxyethylammonium salt, dialkylmethylbenzylammonium salt, and the like, all having an alkyl group derived from Guerbet alcohol. Given as counter-ions for the ammonium salts are halogen ions such as chlorine ion, bromine ion, or iodine ion, or organic anions such as methosulfate, ethosulfate, methophosphate, ethophosphate, or the like. Examples of alkyl groups derived from Guerbet alcohols include 2-hexyldecyl group, 2-octyldodecyl group, 2-decyltetradecyl group, 2-dodecylhexadecyl group, and the like. Particularly preferable examples of branched quaternary ammonium salts of formula(II) are 2-decyltetradecyltrimethylammonium chloride, 2-dodecylhexadecyltrimethylammonium chloride, di-2-hexyldecyldimethylammonium chloride, di-2-octyldodecylammonium chloride, and the like.

These branched quaternary ammonium salts represented by formula (I) or (II) can be employed either individually or in combination. In view of reduced stickiness of the detergent composition quaternary ammonium salts represented by formula (II) are generally preferable.

The amount of the (A) component to be formulated into the detergent composition of this invention is in the range of 0.1 to 40% by weight, and preferably 10 to 25% by weight. Preferable amount of the (B) component is 0.05 to 4%, with especially preferable range being 0.1 to 1% by weight.

Besides the above two essential components, various components commonly known for use in a detergent composition can be formulated. Such components to be added into a shampoo include, for example, noionic surface active agents, moisturizing agent such as propylene glycol, glycerin, and the like, pH adjustment agents such as phosphoric acid, citric acid, and the like, viscosity adjustment agents such as ethanol, higher alcohols, hydroxyethyl cellulose, methyl cellulose, and the like, conditioning agent such as oils or fats of plants or animals origin, and the like, UV ray absorbers, antioxidants, anti-dandruff, antifungals, agents for modifying outward appearance such as pearling agents, and the like. Additives for cloth detergent compositions include foaming agents, de-foaming agents, dirt-reattachment inhibitors, metal ion sealing agents, fluorescents, enzymes, and the like. In addition, antiseptics, coloring agents, perfumes, and the like are formulated as required.

Among the above-mentioned optional ingredients, (C) one or more cationic polymers selected from the group consisting of cationized cellulose derivatives, cationic starch, copolymers of a diallyl quaternary ammonium salt and an acrylamide, quaternarized polyvinylpyrrolidone derivatives, and polyglycol-polyamine condensates, when formulated into the detergent composition, provide even superior conditioning effects.

The compounds represented by the following formula (V) is desirable for use as cationized cellulose derivatives:

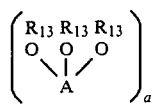 (V)

wherein A represents an anhydrous glucose unit residue, a denotes an integer of 50 to 20,000, and each $R_{13}$ individually represents a group represented by the following formula (VI):

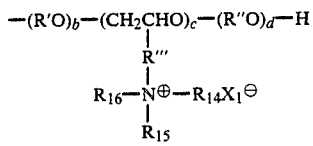 (VI)

wherein R' and R" individually represents an alkylene group having 2 or 3 carbon atoms, b is an integer of 0 to 10, c is an integer of 0 to 3, d is an integer of 0 to 10, R''' represents an alkylene group or a hydroxyalkylene group each having 1 to 3 carbon atoms, $R_{14}$, $R_{15}$, and $R_{16}$ may be the same or different and represent alkyl groups, aryl groups, aralkyl groups, each having not more than 10 carbon atoms, or may form a heterocycle together with the nitrogen atom, and $X_1$ represents an anionic ion (chlorine, bromine, iodine, sulfuric acid, sulfonic acid, methyl sulfate, phosphoric acid, nitric acid, and the like).

A preferable range of the cation substitution degree of cationized cellulose is 0.01 to 1, i.e., in terms of the average value of c for anhydrous glucose 0.01 to 1, and preferably 0.02 to 0.5. The average of b plus d is 1 to 3. A substitution degree of below 0.01 is not sufficient. The value not more than 1 is preferable in view of the reaction yield, although the value above 1 can be acceptable. The molecular weight of the cationic cellulose used is between 100,000 and 3,000,000.

The compounds represented by the following formula (VII) are preferable cationic starches.

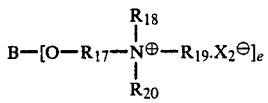 (VII)

wherein B represents a starch residual group, $R_{17}$ represents a alkylene group or a hydroxyalkylene group, $R_{18}$, $R_{19}$, and $R_{20}$ may be the same or different and represent alkyl groups, aryl groups, aralkyl groups, each having not more than 10 carbon atoms, or may form a heterocycle together with the nitrogen atom, $X_2$ represents an anionic ion (chlorine, bromine, iodine, sulfuric acid, sulfonic acid, methyl sulfate, phosphoric acid, nitric acid, and the like), and e is a positive integer.

A preferable range of the cation substitution degree of cationic starch is 0.01 to 1. Specifically, cationic starches having 0.01 to 1, preferably 0.02 to 0.5, cationic group per anhydrous glucose unit are desirable. A substitution degree of below 0.01 is not sufficient. The value not more than 1 is preferable in view of the reaction yield, although the value above 1 can be acceptable.

The compounds represented by the following formula (VIII) or (IX) are preferable as a cationic diallyl quaternary ammonium salt/acryl amide copolymer.

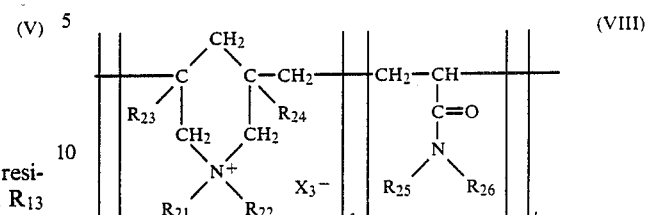 (VIII)

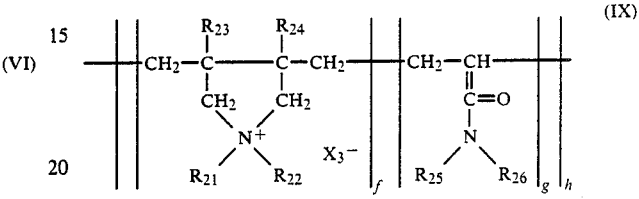 (IX)

wherein $R_{21}$ and $R_{22}$ may be the same or different and represent hydrogen atoms, alkyl groups having 1 to 18 carbon atoms, phenyl groups, aryl groups, hydroxyalkyl groups, amidealkyl groups, cyanoalkyl groups, alcoxyalkyl groups, or carboalcoxyalkyl groups, $R_{23}$, $R_{24}$, $R_{25}$, and $R_{26}$ may be the same or different and represent hydrogen atoms, lower alkyl groups having 1 to 3 carbon atoms, or phenyl groups, $X_3$ represents an anionic ion (chlorine, bromine, iodine, sulfuric acid, sulfonic acid, methyl sulfate, nitric acid, and the like), f is an integer of 1 to 50, g is is an integer of 1 to 50, and h is an integer of 150 to 8,000.

The molecular weight of a diallyl quaternary ammonium salt/acryl amide copolymer is in the range of 30,000 to 2,000,000, and preferably of 100,000 to 1,000,000.

The compounds represented by the following formula (X) are preferable as a quaternarized polyvinylpyrrolidone derivative.

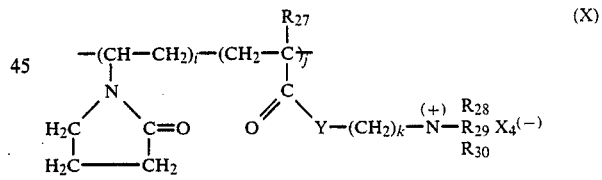 (X)

wherein $R_{27}$ represents a hydrogen atom or a lower alkyl group having 1 to 3 carbon atoms, $R_{28}$, $R_{29}$, and $R_{30}$ may be the same or different and represent hydrogen atoms, alkyl groups having 1 to 4 carbon atoms, hydroxyalkyl groups, amidealkyl groups, cyanoalkyl groups, alcoxyalkyl groups, or carboalcoxyalkyl groups, Y represents an oxygen atom or the NH group of an amide bond, $X_4$ represents an anionic ion (chlorine, bromine, iodine, sulfuric acid, sulfonic acid, alkyl sulfate of a $C_{1-4}$ carbon atom content, phosphoric acid, nitric acid, and the like), k is an integer of 1 to 10, i and j are integers satisfying $i+j=20$ to 8,000.

A molecular weight of a quaternarized polyvinylpyrrolidone derivative is between 10,000 and 2,000,000, with particularly preferable range being between 50,000 and 1,500,000.

The content of the cationic nitrogen originating from cationic polymer in the above vinyl polymer is 0.004 to 0.2%, and preferably 0.01 to 0.15% based on the vinyl polymer. A sufficient effect cannot be expected from the nitrogen atom content of less than 0.004%. On the other hand, the content of above 0.2% causes the vinyl polymer becoming colored and is disadvantageous in view of economy, even though a good performance can be obtained.

Compounds represented by the formula (XI) are preferable as a polyglycol-polyamine condensate.

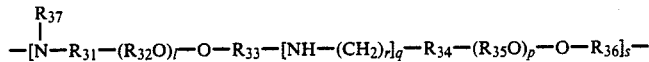

(XI)

wherein $R_{31}$, $R_{33}$, $R_{34}$, and $R_{36}$ represent hydroxyalkylene groups of a $C_{2-4}$ carbon atom content, $R_{32}$ and $R_{35}$ represent alkylene groups of a $C_{2-3}$ carbon atom content, l and p are individually an integer of 10 to 20, q is an integer of 2 to 4, r is an integer of 2 to 6, s is an integer of 1 to 50, $R_{37}$ represents a linear or branched alkyl group of a $C_{6-20}$ carbon atom content.

A copolymer of adipic acid and dimethylaminohydroxypropyldiethylenetriamine (Cartaretine, produced by Sandoz Co., U.S.A.) may also be used as a cationic polymer.

Cationic polymers mentioned above may be used either individually or in combination.

The amount of the (C) component formulated into the detergent composition of this invention is 0.05 to 2% by weight, and particularly preferably 0.1 to 0.8% by weight.

The detergent composition of this invention, when used as a shampoo provides superb hair conditioning effects, such as softness and smoothness after washing, less sticky feeling, easy passage of comb through the hair, less hard or rough feeling as well as easy hair-set performance after drying. The detergent composition also provides a liquid detergent suitable for washing cloths made of keratin fibers such as wool or the like, or made of fine denier fibers, which ensures softness of the cloths after washing.

Other features of the invention will become apparent in the course of the following description of the exemplary embodiments which ar given for illustration of the invention and are not intended to be limiting thereof.

EXAMPLES

In the examples below the following test methods were applied to study the performance of detergent compositions.

(1) Organoleptic evaluation:

Onto a bundle of hair (weight: 20 g, length: 15 cm) of a healthy Japanese woman 1 g of a shampoo was applied. After the shampoo was foamed for 1 minute, the hair bundle was rinsed in a stream of water for 30 seconds. Water was removed from the hair bundle with towel to serve it for organoleptic evaluation with respect to softness and stickiness according to the following criterion:

| Evaluation | Stickiness | Softness |
|---|---|---|
| AAA | Not sticky Dry | — |
| BBB | Not sticky | Soft |
| CCC | Slightly sticky | Slightly soft |
| DDD | Sticky | Not soft |

(2) Passage of comb through the hair

Human hair weighing 30 g was washed in 10 cc of an aqueous solution of a shampoo composition (concentration: 10%) at 40° C. for 30 seconds under shaking. The hair was washed in a water stream for 1 minute, squeezed to remove water, and set to a strain gauge to measure the force applied when combed to obtain a combing force at moistured conditions. Another bundle of hair treated with the same shampoo composition was washed in a water stream, squeezed to remove water, dried with a dryer, and left for overnight in a thermostat container at 25° C. and 65% relative humidity. This bundle of hair was set to a strain gauge to measure the force applied when combed to obtain a combing force at dried conditions. The smaller the load, is easier the combing.

(3) Hair-fly

The same hair used for the measurement of combing force at dried conditions was used for the test, in which the state of hair under electrostatic conditions was observed by naked eyes.

AAA: No hair-fly was occurred

BBB: Occurrence of hair-fly was ob served

EXAMPLE 1

Shampoo compositions listed in Table 1 were prepared and submitted to organoleptic evaluation, evaluation of combing easiness, and of hair-fly. The results are shown in Table 1, in which figures for the composition formulation designate % by weight. Each composition contained, besides components listed in the table, following components:

| Diethanolamide laurate | 3% |
|---|---|
| Perfumes | small amount |
| Water | balance |

As evident from Table 1, shampoos to which cationic polymers or linear quaternary ammonium salts are formulated exhibited only insufficient conditioning effects, while, on the other hand, shampoos to which branched quaternary ammonium salts according to the present invention are formulated exhibited superior performances.

TABLE 1

| | Comparative Composition | | | | | | Invention Composition | | | | | |
|---|---|---|---|---|---|---|---|---|---|---|---|---|
| | 1 | 2 | 3 | 4 | 5 | 6 | 1 | 2 | 3 | 4 | 5 | 6 |
| Sodium polyoxyethylene (2.5) lauryl sulfate | 20 | 10 | 20 | 20 | 20 | 10 | 20 | 15 | 20 | 20 | 15 | 20 |
| Imidazoline-type amphoteric surface active agent*1 | | 10 | | | | 10 | | 5 | | | 5 | |
| Cationic polymer*2 | 0.3 | 0.3 | | | | | | | | | | |
| Cationic polymer*3 | | | 0.3 | | | | | | | | | |

TABLE 1-continued

|  | Comparative Composition | | | | | | Invention Composition | | | | | |
| --- | --- | --- | --- | --- | --- | --- | --- | --- | --- | --- | --- | --- |
|  | 1 | 2 | 3 | 4 | 5 | 6 | 1 | 2 | 3 | 4 | 5 | 6 |
| Cetyltrimethylammonium chloride |  |  |  | 0.3 |  |  |  |  |  |  |  |  |
| Stearyltrimethylammonium chloride |  |  |  |  | 0.3 | 0.3 |  |  |  |  |  |  |
| Dialkyldimethylammonium chloride*4 |  |  |  |  |  |  | 0.3 | 0.3 |  |  |  |  |
| 2-Octyldodecyltrimethyl-ammonium chloride |  |  |  |  |  |  |  |  | 0.3 |  |  |  |
| 2-Decyltetradecyltrimethyl-ammonium chloride |  |  |  |  |  |  |  |  |  | 0.3 | 0.3 |  |
| 2-Dodecylhexadecyltrimethyl-ammonium chloride |  |  |  |  |  |  |  |  |  |  |  | 0.3 |
| Organoleptic evaluation | | | | | | | | | | | | |
| Stickyness | DDD | DDD | CCC | CCC | CCC | CCC | BBB | BBB | BBB | BBB | BBB | AAA |
| Softness | CCC | CCC | DDD | DDD | DDD | DDD | BBB | BBB | BBB | BBB | BBB | BBB |
| Passage of comb | | | | | | | | | | | | |
| Moistured (g) | 287 | 291 | 314 | 315 | 320 | 318 | 226 | 230 | 217 | 213 | 221 | 208 |
| Dried (g) | 185 | 190 | 192 | 205 | 204 | 207 | 142 | 144 | 136 | 130 | 132 | 129 |
| Hair-fly | X | X | X | X | X | X | O | O | O | O | O | O |

*1 Miranol C2M conc. (manufactured by Miranol Co.)
*2 Polymer JR-400 (cationic cellulose, produced by Union Carbide, Inc.)
*3 Marcoat 550 (copolymer of N,N-dimethyl-3,5-methylenepyperidinium chloride and acryl amide, produced by Merck, Inc.
*4 Branched quaternary ammonium salt derived from commercially available oxo alcohol (a mixture of Dovanol 23 and Dovanol 45, both produced by Mitsubishi Petrochemical Co. Ltd., at a weight ratio of 50/50), having a $C_{12-15}$ carbon atom content with a branched degree of 0.2.

EXAMPLE 2

Shampoo compositions listed in Table 2 were prepared and submitted to organoleptic evaluation, and evaluation of hair-fly. The results are shown in Table 2, in which figures for the composition formulation designate % by weight. Each composition contained, besides components listed in the table, following components:

| Diethanolamide laurate | 3% |
| --- | --- |
| Perfumes | small amount |
| Water | balance |
| pH of formulated shampoo composition | 7.0 | shampoos, exhibiting excellent mutual solubility with various anionic or amphoteric surface active agents.

EXAMPLE 3

Shampoo compositions listed in Table 3 were prepared and their performances were evaluated. The results are shown in Table 3, in which figures for the composition formulation designate % by weight. Each composition contained, besides components listed in the table, following components:

| Diethanolamide laurate | 3% |
| --- | --- |
| Perfumes | small amount |
| Water | balance |

TABLE 2

|  | Invention Composition | | | | | | | | | |
| --- | --- | --- | --- | --- | --- | --- | --- | --- | --- | --- |
|  | 7 | 8 | 9 | 10 | 11 | 12 | 13 | 14 | 15 | 16 |
| Sodium polyoxyethylene (2.5) lauryl sulfate |  |  |  |  |  |  | 15 |  | 10 |  |
| Triethanolamine polyoxyethylene (2.5) lauryl sulfate | 20 |  |  |  |  |  |  | 15 |  |  |
| Triethanolamine lauryl sulfate |  | 20 |  |  |  |  |  |  | 10 |  |
| Sodium α-olefin sulfonate |  |  | 20 |  |  |  |  |  |  | 5 |
| Sodium lauroyl-N-methyl-β-alanine |  |  |  | 20 |  |  | 5 |  | 5 |  |
| Imidazoline-type amphoteric surface active agent*1 |  |  |  |  | 20 |  |  | 5 | 5 |  |
| Amidebetaine-type amphoteric surface active agent*5 |  |  |  |  |  | 20 |  | 5 |  |  |
| Dialkyldimethylammonium chloride*4 |  |  |  |  |  |  | 0.5 | 0.5 | 0.5 | 0.5 |
| 2-Dodecylhexadecylammonium chloride | 0.5 | 0.5 | 0.5 | 0.5 | 0.5 | 0.5 |  |  |  |  |
| Organoleptic evaluation | | | | | | | | | | |
| Stickyness | AAA | AAA | AAA | AAA | AAA | AAA | BBB | BBB | BBB | BBB |
| Softness | BBB | BBB | BBB | BBB | BBB | BBB | BBB | BBB | BBB | BBB |
| Hair-fly | O | O | O | O | O | O | O | O | O | O |

*1 Miranol C2M conc. (manufactured by Miranol Co.)
*4 Branched quaternary ammonium salt derived from commercially available oxo alcohol (a mixture of Dovanol 23 and Dovanol 45, both produced by Mitsubishi Petrochemical Co. Ltd., at a weight ratio of 50/50), having a $C_{12-15}$ carbon atom content, with a branched degree of 0.2.
*5 Revon 2000 (manufactured by Sanyo chemical Co. Ltd.)

As evident from Table 2, branched quaternary ammonium salts contributed to superior performances of

| pH of formulated shampoo composition | 7.0 |
| --- | --- |

TABLE 3

|  | Comparative Composition | | | | Inventive Composition | | | | | | | |
|---|---|---|---|---|---|---|---|---|---|---|---|---|
|  | 7 | 8 | 9 | 10 | 17 | 18 | 19 | 20 | 21 | 22 | 23 | 24 |
| Triethanolamine polyoxyethylene (2.5) lauryl sulfate | 18 | 18 | 18 | 18 | 18 | 18 | 18 | 18 | 18 | 18 | 18 | 18 |
| Dialkyldimethylammonium chloride*4 | 0.01 | 5 |  |  | 0.05 | 0.5 | 1 | 2 | 3 | 4 |  |  |
| 2-Octyldodecyltrimethyl ammonium chlorde |  |  | 0.01 | 5 |  |  |  |  |  |  | 0.05 | 4 |
| Organoleptic evaluation |  |  |  |  |  |  |  |  |  |  |  |  |
| Stickyness | BBB | DDD | BBB | DDD | BBB | BBB | BBB | BBB | BBB | BBB | BBB | BBB |
| Softness | CCC | BBB | CCC | BBB | BBB | BBB | BBB | BBB | BBB | BBB | BBB | BBB |
| Hair-fly | X | O | X | O | O | O | O | O | O | O | O | O |

*4 Branched quaternary ammonium salt derived from commercially available oxo alcohol (a mixture of Dovanol 23 and Dovanol 45, both produced by Mitsubishi Petrochemical Co. Ltd., at a weight ratio of 50/50), having a $C_{12-15}$ carbon atom content with a branched degree of 0.2.

Table 3 demonstrates that with the amount of formulation of a branched quaternary ammonium salt at less than 0.05% by weight, the conditioning effect is low, while the amount exceeding 4.0% by weight caused stickiness and impaired passage of fingers through the hair.

EXAMPLE 4

Shampoo compositions listed in Tables 4-1 and 4-2 were prepared and their organoleptic feeling, passage of comb, and hair-fly were evaluated. The results are shown in Tables 4-1 and 4-2, in which figures for the composition formulation designate % by weight. Each composition contained, besides components listed in the table, following components:

| Diethanolamide laurate | 3% |
|---|---|
| Perfumes | small amount |
| Water | balance |
| pH of formulated shampoo composition | 7.0 |

TABLE 4-1

|  | Comparative Composition | | | | | Invention Composition | | | |
|---|---|---|---|---|---|---|---|---|---|
|  | 11 | 12 | 13 | 14 | 15 | 25 | 26 | 27 | 28 |
| N-lauroyl-N'-carboxymethyl-N'-(2-hydroxyethyl)ethylenediamine triethylammonium | 20 |  | 10 | 10 |  | 20 | 20 | 20 | 20 |
| N-lauroyl-N-(2-hydroxyethyl)-N',N'-bis(carboxymethyl)-ethylenediamine triethylammonium |  | 20 |  |  | 10 |  |  |  |  |
| Polyoxyethylene (2.5) lauryl sulfate triethylammonium |  |  | 10 | 10 | 10 |  |  |  |  |
| Cationic polymer 1 *1 | 0.5 | 0.5 |  |  |  | 0.3 | 0.3 | 0.3 | 0.3 |
| Cationic polymer 2 *2 |  |  | 0.5 |  |  |  |  |  |  |
| Cationic polymer 3 *3 |  |  |  | 0.5 |  |  |  |  |  |
| Cationic polymer 4 *4 |  |  |  |  | 0.5 |  |  |  |  |
| Dialkyldimethylammonium chloride *5 |  |  |  |  |  | 0.2 |  |  |  |
| 2-Octyldodecyltrimethyl ammonium chloride |  |  |  |  |  |  | 0.2 |  |  |
| 2-Decyltetradecyltrimethyl-ammonium chloride |  |  |  |  |  |  |  | 0.2 |  |
| 2-Dodecylhaexadecyltrimethyl-ammonium chloride |  |  |  |  |  |  |  |  | 0.2 |
| Organoleptic evaluation |  |  |  |  |  |  |  |  |  |
| Stickyness | DDD | DDD | CCC | CCC | CCC | BBB | BBB | BBB | AAA |
| Softness | CCC | CCC | DDD | DDD | DDD | BBB | BBB | BBB | BBB |
| Passage of comb |  |  |  |  |  |  |  |  |  |
| Moistured | 298 | 306 | 322 | 319 | 327 | 231 | 227 | 229 | 214 |
| Dried | 187 | 192 | 205 | 200 | 203 | 143 | 138 | 132 | 125 |
| Hair-fly | X | X | X | X | X | O | O | O | O |

TABLE 4-2

|  | Invention Composition | | | | | | | | |
|---|---|---|---|---|---|---|---|---|---|
|  | 29 | 30 | 31 | 32 | 33 | 34 | 35 | 36 | 37 |
| N-lauroyl-N'-carboxymethyl-N'-(2-hydroxyethyl)ethylenediamine triethylammonium | 10 | 10 | 10 |  |  | 10 | 10 | 5 | 5 |
| N-lauroyl-N-(2-hydroxyethyl)-N',N'-bis(carboxymethyl)-ethylendiamine triethylammonium |  |  |  | 10 | 20 |  |  |  |  |
| Polyoxyethylene (2.5) lauryl sulfate triethylammonium | 10 | 10 | 10 | 10 |  | 10 | 10 | 15 | 15 |
| Cationic polymer 1 *1 |  |  |  |  | 0.3 | 0.3 | 0.1 | 0.1 | 0.7 | 0.7 |
| Cationic polymer 2 *2 | 0.3 |  |  |  |  |  |  |  |  |
| Cationic polymer 3 *3 |  | 0.3 |  |  |  |  |  |  |  |
| Cationic polymer 4 *4 |  |  | 0.3 |  |  |  |  |  |  |
| Dialkyldimethylammonium |  |  |  |  | 0.2 |  |  |  |  |

TABLE 4-2-continued

| | Invention Composition | | | | | | | | |
|---|---|---|---|---|---|---|---|---|---|
| | 29 | 30 | 31 | 32 | 33 | 34 | 35 | 36 | 37 |
| chloride *5 | | | | | | | | | |
| 2-Octyldodecyltrimethyl ammonium chloride | | | | | | | | | |
| 2-Decyltetradecyltrimethyl- ammonium chloride | | | | | | | | | |
| 2-Dodecylhaexadecyltrimethyl- ammonium chloride | 0.2 | 0.2 | 0.2 | | 0.2 | 0.05 | 0.5 | 0.05 | 0.3 |
| Organoleptic evaluation | | | | | | | | | |
| Stickyness | AAA | AAA | AAA | BBB | BBB | BBB | AAA | BBB | AAA |
| Softness | BBB | BBB | BBB | BBB | BBB | BBB | BBB | BBB | BBB |
| Passage of comb | | | | | | | | | |
| Moistured (g) | 225 | 230 | 219 | 234 | 241 | 250 | 232 | 205 | 200 |
| Dried (g) | 127 | 137 | 132 | 141 | 136 | 146 | 133 | 119 | 114 |
| Hair-fly | O | O | O | O | O | O | O | O | O |

*1 Polymer JR-400 (cationic cellulose, produced by Union Carbide, Inc.)
*2 A cationic starch
*3 Marcoat 550 (copolymer of N,N-dimethyl-3,5-methylenepyperidinium chloride and acryl amide, produced by Merck, Inc.)
*4 Quaternalized ethyl sulfate of vinylpyrrolidone-dimethylaminoethyl acrylate copolymer (Gufcoat 775N, produced by Guf Co.)
*5 Branched quaternary ammonium salt derived from commercially available oxo alcohol (a mixture of Dovanol 23 and Dovanol 45, both produced by Mitsubishi Petrochemical Co. Ltd., at a weight ratio of 50/50), having a $C_{13-15}$ carbon atom content, with a branched degree of 0.2.

EXAMPLE 5

Shampoo compositions of the following formulations were prepared and subjected to organoleptic evaluation by ten women with long hairs. The results are shown in Table 5.

| Component | % by weight |
|---|---|
| Shampoo A (Invention Product): | |
| Sodium N-lauroyl-N'-carboxymethyl-N'-(2-hydroxyethyl)ethylene-diamine | 15 |
| Diethanolamide laurate | 3 |
| Cationic polymer (Polymer JR-400; manufactured by Union Carbide Corp.) | 0.3 |
| 2-Dodecylhexadecyltrimethyl ammonium chloride | 0.2 |
| Antiseptics | 0.1 |
| Perfumes | 0.4 |
| Coloring agent | small amount |
| Water | balance |
| pH | 7 |
| Shampoo B (comparative Product): | |
| Sodium N-lauroyl-N'-carboxymethyl-N'-(2-hydroxyethyl)ethylene-diamine | 15 |
| Diethanolamide laurate | 3 |
| Cationic polymer (Polymer JR-400; manufactured by Union Carbide Corp.) | 0.3 |
| Antiseptics | 0.1 |
| Perfumes | 0.4 |
| Coloring agent | small amount |
| Water | balance |
| pH | 7 |

TABLE 5

| | Shampoo A was better | Shampoo B was better | Could not tell difference |
|---|---|---|---|
| Amount of foam | 3 | 2 | 5 |
| Finger passage through the hair | 6 | 2 | 2 |
| Smoothness after rinse | 8 | 2 | 0 |
| Softness after rinse | 7 | 3 | 0 |
| Brushing easiness while blow drying | 9 | 1 | 0 |
| Easiness of hair-set after drying | 9 | 1 | 0 |
| Comb passage through the hair after drying | 8 | 1 | 1 |

EXAMPLE 6-8

Shampoo compositions having following formulations were prepared. All these compositions produced abundant foam, removed dirt efficiently, and provided an excellent soft feeing after hair-washing.

EXAMPLE 6

| Shampoo: | |
|---|---|
| Component | % by weight |
| Triethanolamine lauryl sulfate | 16 |
| Sodium lauroylsarcosine | 3 |
| Diethanol amide laurate | 2 |
| 2-Decyltetradecyltrimethylammonium chloride | 0.5 |
| Antiseptics | 0.1 |
| Perfumes, Coloring agents | (appropriate amount) |
| Water | balance |
| | 100 |

EXAMPLE 7

| Shampoo: | |
|---|---|
| Component | % by weight |
| Triethanolamine lauryl phosphate | 18 |
| Laurylhydroxysulfobetaine | 3 |
| Monoethanol amide laurate | 1 |
| Dialkyldimethylammonium chloride | 0.7 |
| Antiseptics | 0.1 |
| Pearling agents | 5 |
| Perfumes, Coloring agents | (appropriate amount) |
| Water | balance |
| | 100 |

EXAMPLE 8

Shampoo:

| Component | % by weight |
|---|---|
| Sodium polyoxyethylene (3.0) lauryl sulfate | 7 |
| Carbobetaine | 5 |
| Sodium lauroyl-N-methyl-β-alanine | 2 |
| Cationic polymer (Polymer JR-400; manufactured by Union Carbide Corp.) | 0.2 |
| 2-Dodecylhexadecyltrimethylammonium chloride | 0.4 |
| Antiseptics | 0.1 |
| Perfumes, Coloring agents | (appropriate amount) |
| Water | balance |
| | 100 |

EXAMPLE 9

A liquid light detergent for clothing of the following formulation was prepared. A wool sweater was hand-washed with a 0.25% aqueous solution, rinsed, and dried. The wool sweater had an excellent smooth, soft feeling.

| Component | % by weight |
|---|---|
| Sodium linear alkyl ($\bar{c}$ = 12.5) benzene sulfonate | 10 |
| Polyoxyethylene ($\bar{p}$ = 10) lauryl ether | 10 |
| 2-Octyldodecyltrimethylammonium chloride | 2 |
| Sodium citrate dihydride | 5 |
| Perfumes | small amount |
| Water | balance |
| | 100 |

EXAMPLES 10–13

Shampoos having the following formulations exhibited only very weak stimulus to the skin and provided a soft finished feeling after washing.

EXAMPLE 10

| Component | % by weight |
|---|---|
| Sodium N-lauroyl-N-(2-hydroxyethyl)-N',N'-bis(carboxyethyl) ethylenediamine | 12 |
| Sodium polyoxyethylene (2.5) laurylether sulfate | 5 |
| Diethanolamide laurate | 3 |
| Cationic polymer (Marcoat 550; produced by Merck Co.) | 0.2 |
| 2-Decyltetradecyltrimethylammonium chloride | 0.2 |
| Antiseptics | 0.1 |
| Perfumes, Coloring agents | (appropriate amount) |
| Water | balance |
| | 100 |

EXAMPLE 11

| Component | % by weight |
|---|---|
| N-lauroyl-N'-carboxymethyl-N'-(2-hydroxyethyl)-ethylenediamine triethanolamine | 3 |
| Laurylether sulfate triethanolamine | 15 |
| Diethanolamide laurate | 2 |
| Cationic polymer (Polymer JR-400; manufactured by Union Carbide Corp.) | 0.6 |
| Dialkyldimethylammonium chloride | 0.1 |
| Antiseptics | 0.1 |
| Perfumes, Coloring agents | (appropriate amount) |
| Water | balance |
| | 100 |

EXAMPLE 12

| Component | % by weight |
|---|---|
| N-lauroyl-N'-carboxymethyl-N'-(2-hydroxyethyl)-ethylenediamine triethanolamine | 18 |
| Polyoxyethylene (2.5) laurylether sulfate triethanolamine | 5 |
| Ethanolamine salt of 1-hydroxy-4-methyl-6-(2,4,4-trimethylphenyl)-2(1H)-pyridinone (Octopyrox) | 1 |
| Cationic polymer (Polymer JR-400; manufactured by Union Carbide Corp.) | 0.1 |
| 2-Dodecylhexadecyltrimethylammonium chloride | 0.2 |
| Methyl cellulose | 0.3 |
| Antiseptics | 0.1 |
| Perfumes, Coloring agents | (appropriate amount) |
| Water | balance |
| | 100 |

EXAMPLE 13

| Component | % by weight |
|---|---|
| Sodium N-lauroyl-N-(2-hydroxyethyl)-N',N'-bis(carboxyethyl) ethylenediamine | 0.8 |
| Sodium polyoxyethylene (3.0) laurylether sulfate | 18 |
| Cationic polymer (Gafcoat 755N, produced by Guf Co.) | 0.4 |
| 2-Dodecylhexadecyltrimethylammonium chloride | 0.3 |
| Antiseptics | 0.1 |
| Pearling agents | 5 |
| Perfumes, Coloring agents | appropriate amount |
| Water | balance |
| | 100 |

Obviously, numerous modifications and variations of the present invention are possible in light of the above teachings. It is therefore to be understood that the scope of the appended claims, the invention may be practiced otherwise than as specifically described herein.

What is claimed as new and desired to be secured by Letters Patent:

1. A detergent composition comprising:
   (A) 0.1 to 40% by weight of at least one kind of anionic or amphoteric surface active agents and
   (B) 0.05 to 4% by weight of at least one kind of quaternary ammonium salts represented by the following formula (I) or (II):

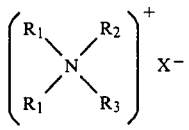 (I)

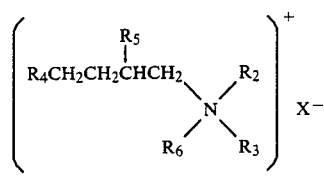 (II)

wherein $R_1$ represents a mixture of (a) a branched alkyl group represented by

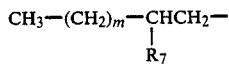

and (b) a linear alkyl group represented by $CH_3-(CH_2)_n-$ (wherein $R_7$ represents a methyl or ethyl group, m is an integer to make the carbon atom content of the branched alkyl group to 8 to 16, and n is an integer of 7 to 15), with a ratio (a)/(a)+(b) being 0.1 to 1, $R_2$ and $R_3$ independently represent a benzyl group, an alkyl group having 1 to 3 carbon atoms, or a hydroxyalkyl group having 1 to 3 carbon atoms, $R_4$ and $R_5$ independently represent an alkyl group having 2 to 12 carbon atoms, $R_6$ represents a group

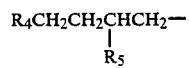

or an alkyl group having 1 to 3 carbon atoms, and X represents a halogen ion or an organic anion.

2. A detergent composition comprising:
(A) 0.1 to 40% by weight of at least one kind of anionic or amphoteric surface active agents,
(B) 0.05 to 4% by weight of at least one kind of quaternary ammonium salts represented by the following formula (I) or (II):

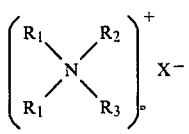 (I)

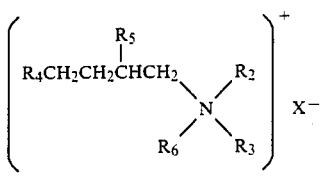 (II)

wherein $R_1$ represents a mixture of (a) a branched alkyl group represented by

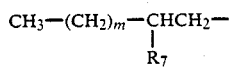

and (b) a linear alkyl group represented by $CH_3-(CH_2)_n-$ (wherein $R_7$ represents a methyl or ethyl group, m is an integer to make the carbon atom content of the branched alkyl group to 8 to 16, and n is an integer of 7 to 15), with a ratio (a)/(a)+(b) being 0.1 to 1, $R_2$ and $R_3$ independently represent a benzyl group, an alkyl group having 1 to 3 carbon atoms, or a hydroxyalkyl group having 1 to 3 carbon atoms, $R_4$ and $R_5$ independently represent an alkyl group having 2 to 12 carbon atoms, $R_6$ represents a group

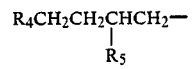

or an alkyl group having 1 to 3 carbon atoms, and $X^-$ represents a halogen ion or an organic anion, and
(C) 0.05 to 2% by weight of at least one cationic polymer selected from the group consisting of cationized cellulose derivatives, cationic starch, copolymers of a diallyl quaternary ammonium salt and an acrylamide, quaternarized polyvinylpyrrolidone derivatives, and polyglycol-polyamine condensate.

3. The detergent composition according to claim 2, wherein 0.1 to 25% by weight, based on said detergent composition, of said (A) component is one or more amidoamine-type amphoteric surface active agents represented by the following formula (III) or (IV):

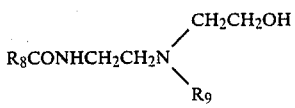 (III)

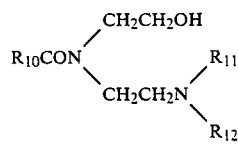 (IV)

wherein $R_8$ and $R_{10}$ each independently represent a saturated or unsaturated hydrocarbon group having 7 to 19 carbon atoms, $R_9$ and $R_{11}$ each independently represent a group $-CH_2COOM$ or $-CH_2CH_2COOM$ (wherein M stands for a hydrogen atom, an alkali metal, or an alkanol amine), $R_{12}$ represents a hydrogen atom, a group $-CH_2COOM$, or a group $-CH_2CH_2COOM$ (wherein M has the same meaning as defined above).

* * * * *